(12) United States Patent
Fischer et al.

(10) Patent No.: US 9,797,818 B2
(45) Date of Patent: Oct. 24, 2017

(54) TESTING DEVICE FOR TESTING SEALS HAVING ANCHORING FEET

(71) Applicant: Daetwyler Sealing Technologies Deutschland GmbH, Walterhausen (DE)

(72) Inventors: Mark Fischer, Hoersel OT Teuleben (DE); Oliver Pasemann, Eisenach (DE); Matthias Stender, Gotha (DE)

(73) Assignee: Daetwyler Sealing Technologies Deutschland GmbH, Waltershausen (DE)

( * ) Notice: Subject to any disclaimer, the term of this patent is extended or adjusted under 35 U.S.C. 154(b) by 46 days.

(21) Appl. No.: 14/915,712

(22) PCT Filed: Sep. 9, 2014

(86) PCT No.: PCT/DE2014/200461
§ 371 (c)(1),
(2) Date: Mar. 1, 2016

(87) PCT Pub. No.: WO2015/035994
PCT Pub. Date: Mar. 19, 2015

(65) Prior Publication Data
US 2016/0195459 A1  Jul. 7, 2016

(30) Foreign Application Priority Data

Sep. 13, 2013 (DE) .................... 10 2013 218 447
Oct. 1, 2013 (DE) .................... 10 2013 110 928

(51) Int. Cl.
*E21D 11/38* (2006.01)
*F16J 15/06* (2006.01)
(Continued)

(52) U.S. Cl.
CPC ............. *G01N 3/02* (2013.01); *E21D 11/385* (2013.01); *G01M 3/02* (2013.01); *G01M 5/0058* (2013.01); *G01N 3/08* (2013.01)

(58) Field of Classification Search
CPC ....... E21D 11/00; E21D 11/38; E21D 11/385; F16J 15/00; F16J 15/02; F16J 15/06;
(Continued)

(56) References Cited

U.S. PATENT DOCUMENTS 4,002,055 A    1/1977  Kops
4,195,850 A *  4/1980  Berger .................. E04B 1/6812
                                                     277/650

(Continued)

FOREIGN PATENT DOCUMENTS

DE    4231896 A1    3/1994
DE    4232794 A1    3/1994
(Continued)

OTHER PUBLICATIONS

Singapore Office Action dated Mar. 20, 2017, in Singapore Patent Application No. 11201601121W.
(Continued)

*Primary Examiner* — Nguyen Ha
*Assistant Examiner* — 'Wyn' Ha
(74) *Attorney, Agent, or Firm* — Patent Central LLC; Stephan A. Pendorf

(57) ABSTRACT

A testing device for testing seals, in particular tubbing seals, which seals have at least one anchoring foot. The testing device can be easily and cost-effectively adjusted to various seals by using plates with a recess, in which correspondingly configured plate elements are detachably inserted, so that different groove shapes scan be reproduced. The recess thus acts as a kind of "universal groove", which can be adjusted to the respective geometry of the sealing profile to be tested (Continued)

by means of the plate elements, if necessary with the assistance of a curing or curable material.

9 Claims, 4 Drawing Sheets

(51) Int. Cl.
*G01N 3/02* (2006.01)
*G01M 5/00* (2006.01)
*G01M 3/02* (2006.01)
*G01N 3/08* (2006.01)

(58) Field of Classification Search
CPC ........ G01M 3/02; G01M 3/08; G01M 5/0058; G01N 3/02; G01N 3/08
See application file for complete search history.

(56) References Cited

U.S. PATENT DOCUMENTS

| | | | |
|---|---|---|---|
| 4,445,387 A | | 5/1984 | Hall et al. |
| 4,834,395 A * | | 5/1989 | Benford ................ B29C 70/845 264/46.8 |
| 5,074,711 A * | | 12/1991 | Glang ................... E21D 11/385 277/625 |
| 5,297,441 A | | 3/1994 | Smith et al. |
| 6,052,960 A * | | 4/2000 | Yonemura ................ E02D 5/14 404/47 |
| 7,118,137 B2 | | 10/2006 | Deremiah ............. F16L 21/035 285/305 |
| 7,766,341 B2 * | | 8/2010 | Okumura ............... F16J 15/104 277/606 |
| 8,604,799 B2 | | 12/2013 | Roedel et al. |
| 2003/0168819 A1 * | | 9/2003 | Gutschmidt .......... E21D 11/385 277/628 |
| 2012/0301224 A1 * | | 11/2012 | Peters ..................... E21D 11/08 405/152 |
| 2012/0328369 A1 * | | 12/2012 | Hoeft .................... E21D 11/385 405/152 |

FOREIGN PATENT DOCUMENTS

| | | |
|---|---|---|
| DE | 8916280 U1 | 1/1997 |
| DE | 7515943 U | 3/1997 |
| DE | 10222032 A1 | 12/2002 |
| DE | 69716956 T2 | 8/2003 |

OTHER PUBLICATIONS

Flath, Thomas et al: "STUVA-Empfehlung für die Prüfung und den Einsatz von Dichtungsprofilen in Tübbingauskleidungen", Jan. 1, 2005 (Jan. 1, 2005), pp. 8-21, XP055183530, Retrieved from the internet: URL:http://www.stuvatec.de/dokumente/STUVA-Empfehlung_REC_8_2005_02.pdf [retrieved on Apr. 16, 2015], the whole document.

Flath, Thomas et al.: "STUVA-Empfehlung für die Verwendung von Dichtungsrahmen in Tübbingauskleidungen", Tunnel Feb. 2006, Jan. 1, 2006 (Jan. 1, 2006), pp. 28-33, XP055183905, Retrieved from the Internet: URL:http://www.stuvatec.de/dokumente/STUVA-Empfehlung_REC_2_2006_02.pdf, [retrieved on Apr. 17, 2015] p. 30, paragraph 4.

Schreyer, Joerg: "Abdichtungen von einschaligen Tübbingauskleidungen mit Dichtungsprofilen", Unterirdisches Bauen 2001, Forschung und Praxis 39, Jan. 1, 2001 (Jan. 1, 2001), pp. 142-149, XP055183519, Köln, Germany, Retrieved from the Internet: URL:http://www.stuvatec.de/dokumente/Schreyer_Abdichtung_einschaliger_Tunnelauskleidungen.pdf [retrieved on Apr. 16, 2015], the whole document.

International Search Report and Written Opinion dated Apr. 28, 2015, in International Application No. PCT/DE2014/200461.

Daub "Concrete Linings for Tunnels built by underground construction"—"Betonauskleidungen für Tunnel in geschlossener Bauweise" Tunnel, Mar. 2001, pp. 27-43.

International Preliminary Report on Patentability dated Mar. 15, 2016, in International Application No. PCT/DE2014/200416.

* cited by examiner

TESTING DEVICE FOR TESTING SEALS HAVING ANCHORING FEET

BACKGROUND OF THE INVENTION

Field of the Invention

The invention relates to a testing device for testing seals, in particular tubbing segment seals, with at least one anchoring foot, the use of the testing device, and a method for testing seals with at least one anchoring foot.

Description of the Related Art

Testing devices for testing seals used in shaft or tunnel constructions, for example sealing profiles of tubbing segments, are basically known (e.g., see Schreyer, Jörg, 2001, Seals of Tubbing Segment Linings with Sealing Profiles, In: Studiengesellschaft für Unterirdische Verkehrsanlagen e.V. (STUVA) (German Research Organization for Underground Transportation), Cologne (publisher), Underground Construction 2001, Research and Practice 39, pp. 142-149; Flath, T. et al., 2005, STUVA Recommendation for the Testing and Use of Sealing Profiles in Tubbing Segment Linings, TUNNEL August 2005; http://www.stuvatec.de/stuvatec-02_036.htm).

In order to test seals with anchoring feet, such as those often used in tunnel construction, it has previously been necessary to manufacture concrete test specimens suitable only for testing purposes, in which the seals are anchored, which is very material, time and cost-intensive. Another disadvantage is that concrete test specimens adjusted specifically to different seals had to be fabricated, so that corresponding molds had to be kept available for this purpose as well, for example. The realization of practical tests on a T-joint or cross joint with test specimens made out of concrete has thus far only been possible at an enormous expense, and is thus not yet possible from a practical standpoint.

The object of the present invention is to improve the possibilities for testing seals, in particular tubbing segment seals, with anchoring feet.

BRIEF SUMMARY OF THE INVENTION

The testing device provided by the present invention for testing seals, in particular tubbing segment seals, with at least one anchoring foot, comprises at least a first plate with a first surface exhibiting a first recess, and at least a second plate with a second surface exhibiting a second recess, wherein the surfaces of the plates lie essentially opposite each other at least partially with their recesses, and wherein at least two respective plate elements are detachably secured in the first and second recess, wherein the plate elements are configured and arranged in such a way as to, if necessary with the inclusion of the wall or portions of the wall of the recesses, form a respective groove in the recesses, in which a seal exhibiting at least one anchoring foot can be inserted, such that the seal is anchored by means of a positive-locking fit formed between the plate elements and the at least one anchoring foot, or a space is formed between the plate elements and the at least one anchoring foot of the seal, into which a curing or curable material can be introduced, so that, after the material has cured, the seal is anchored by means of a positive-locking fit formed between the plate elements, the cured material and the at least one anchoring foot.

The underlying idea of the invention is to provide a testing device that can be easily and cost-effectively adjusted to various seals by using plates with a recess, in which correspondingly configured plate elements are detachably inserted, so that different groove shapes scan be reproduced. The recess thus acts as a kind of "universal groove", which can be adjusted to the respective geometry of the sealing profile to be tested by means of the plate elements, if necessary with the assistance of a curing or curable material. The plate elements simultaneously also serve to positively anchor seals with anchoring feet directly, i.e., through direct contact between the plate elements and the anchoring feet, or indirectly, i.e., via the curing or curable material. This makes it possible to use a testing device for various sealing profiles and repeatedly. All that must be done is to insert a set of plate elements in the recess that are adjusted to the respective geometry of the sealing profile, or that form a space between the plate elements and the seal or its anchoring foot/anchoring feet, in which the curing or curable material can be introduced, so that the cured material indirectly establishes a positive-locking fit between the plate elements and anchoring foot/anchoring feet. For example, testing devices made out of metal (e.g., steel) or even plastic can be used as a result. Complete concrete test specimens need not be cast.

In the testing device according to the invention with such a flexibly insertable accommodating and fastening system for in particular thread-like seals with anchoring feet, at least two plate elements are provided, which can be used to reproduce a groove for a seal with at least one anchoring foot in the recess, or form a space for accommodating the curing or curable material. The edge surfaces of the plate elements form a groove inside of the recess, into which a seal with at least one anchoring foot can be placed. In an embodiment, the at least one anchoring foot is here encased by the plate elements in such a way that the seal is anchored in the plate. Instead of being embedded in concrete, the anchoring foot in this embodiment is enveloped by the plate elements, and the seal is anchored in this way, thereby simulating a test situation of the kind that would be present for a concrete test specimen according to prior art. In an alternative embodiment, the at least one anchoring foot and the plate elements have located between them a gap, into which a curing or curable material can be introduced, so that the seal is anchored after the material has cured. This alternative embodiment makes it possible to simulate a situation that reflects the subsequent installation situation even more closely, for example in a concrete tubbing segment. In one configuration of this alternative embodiment of the testing device according to the invention, the plate elements can be designed in such a way as to essentially follow the geometry of the seal in the area of the anchoring feet, but a gap that can be filled with the curing or curable material here remains between the plate elements and anchoring feet. In other embodiments, the configuration of plate elements can be oriented solely toward an effective positive-locking fit, and hence a sufficient anchoring of the seal, coming about. For example, this can be achieved via undercuts, recesses and the like in the plate element surfaces facing the anchoring feet.

The testing device according to the invention can be adjusted in terms of its configuration relative to various test situations. For example, the testing device can be configured for testing the force-distance behavior of simple sealing threads or frame corners, or also for testing the tightness of sealing frames.

In a preferred embodiment, at least three plate elements are present, for example for the frequent case of a seal having two anchoring feet. Two outer plate elements and a third plate element situated in between here form a groove, into which a seal with two anchoring feet can be inserted, and also simultaneously anchored by the plate elements via a positive-locking fit. Additional plate elements can also be provided given more complicated geometries. The plate elements can each be one-piece or multi-piece, i.e., consist of a respective one or several individual parts. Alternatively, the outer plate elements can form a respective space between the surfaces of the plate elements directed toward the seal and the flanks of the two anchoring feet directed toward the plate elements. A curing or curable material is introduced into the space, and used to anchor the seal once in the cured state.

The term "anchoring foot" is here understood as a seal extension, which projects into a subsequent molded part, e.g., concrete molded part, and establishes a positive-locking fit between the profile and molded part, so that the profile is fastened to or in the cured molded part in such a way that it cannot be removed without damaging the molded part and/or the profile (e.g., by tearing away the profile extension). To this end, for example, the profile extensions can have a dovetailed configuration or generally be provided with a cross section that increases toward the distal extension end. Alternatively or additionally, an anchoring foot can also be provided with a barb; undercuts and the like.

A "T-joint" here refers to a situation in which joints, e.g., ring and longitudinal joints of tunnel tubbing segments, abut against each other in such a way as to result in a T-shaped joint. Accordingly, a "cross joint" refers to a situation in which a cross-shaped joint is formed between the tubbing segments.

As opposed to a "picture frame corner", a "real frame corner" refers to a corner in a sealing profile in which a strand-shaped sealing profile is angled toward the profile base. By contrast, a "picture frame corner" is a corner that arises when a strand-shaped sealing profile is angled toward one of the lateral flanks.

A "curing or curable material" is here understood as an initially flowable material, but one that later cures by itself under normal conditions or when exposed to an outside influence, e.g., heat, UV light, etc. For example, this can be concrete, synthetic resin, adhesive and the like.

The plate elements are detachably secured in the recess. For example, this can be done through screwing, latching, bonding or the like. In order to insert the seal, it may be necessary to initially fix only a portion of the plate elements, e.g., the third plate element, in the recess, then insert the seal, and subsequently to arrange and fix the remaining, e.g., lateral plate elements, for final anchoring.

The surfaces of the outer plate elements facing away from the seal preferably lie on the opposing lateral walls of the recess. In those frequent cases where strand-shaped sealing profiles are to be tested, the recess and plate elements are preferably also essentially strand-shaped in design.

For example, the testing device according to the invention can encompass two planar plates, in whose one surface a respective corresponding recess is introduced, in which the respectively corresponding plate elements are inserted. In order to perform the test, a seal is inserted into each groove formed by the plate elements, and either directly or indirectly anchored via the plate elements in the groove by means of a curing or curable material, e.g., concrete, the plates are placed against each other with the surfaces encompassing the recesses, so that the plates are arranged plane parallel, and the seals come to lie against each other with their sealing surfaces, and are pressed together. For pressing purposes, the testing device according to the invention preferably exhibits corresponding arrangements, which can be used to press the plates against each other. For example, such a testing device can be used for testing the force-distance behavior of a strand-shaped sealing profile. A tightness check can also be performed with a testing device constructed according to the invention by using a sealing frame. To this end, the recesses in the plate surfaces are also designed as frames, and the plate elements form a frame-like groove correspondingly adjusted to the sealing geometry. For example, two boreholes through one of the plates can be used to guide water in the gap bordered by the sealing frame between the plates, and a tightness check can be performed by applying a suitable counter-pressure.

The testing device can be used for testing a seal offset. For example, different sets of plate elements can be used for this purpose, so that the seal is offset in a plate in relation to the seal in the opposing plate. Of course, such an offset situation can be created by offsetting the plates or recesses themselves.

In a preferred embodiment, the testing device according to the invention encompasses at least three plates, wherein the first plate is planar, and the second and third plate are angled, so that the second and third plates exhibit two respective legs situated at a right angle to each other, and wherein the second and third plates are arranged in such a way that the surfaces of the one leg face each other and the surfaces of the other leg face the surface of the first plate, wherein reference is here made to the surfaces that contain the recesses. This yields a testing device with essentially a T-shaped cross section, for example which is suitable for testing the force-distance behavior or the tightness of a seal given an installation situation involving T-joints. In such a T-joint installation situation, the tightness of a seal is checked by inserting a planar, frame-like sealing profile in the groove of the first plate, while a respective sealing frame with two real frame corners is inserted into the grooves of the second and third plate, in order to simulate the situation for tubbing segment seals that abut against each other in a T-joint.

Of course, the present invention also encompasses embodiments with more than three plates. For example, a construction with four angle plates is conceivable, so that a testing arrangement can be manufactured that simulates a situation involving a cross-joint.

The invention also relates to the use of a testing device according to the invention for checking tightness or testing the force-distance behavior of seals with anchoring feet, in particular tubbing segment seals, constructed with T-joints or cross-joints.

In addition, the invention also relates to a method for testing seals with anchoring feet, in particular tubbing segment seals, constructed with T-joints or cross-joints, wherein a seal exhibiting at least one anchoring foot is anchored in a testing device according to the invention, and subjected to a test for tightness or force-distance behavior. To this end, the seal is anchored in the testing device in a suitable manner as described above, for example by introducing a fluid into the testing device, pressurized to check the tightness, and/or examined for its force-distance behavior by pressing together the plates of the testing device.

BRIEF DESCRIPTION OF THE SEVERAL VIEWS OF THE DRAWINGS

The invention will be explained in greater detail below based on the attached figures, strictly for illustrative purposes.

DETAILED DESCRIPTION OF THE INVENTION

Figure 1:
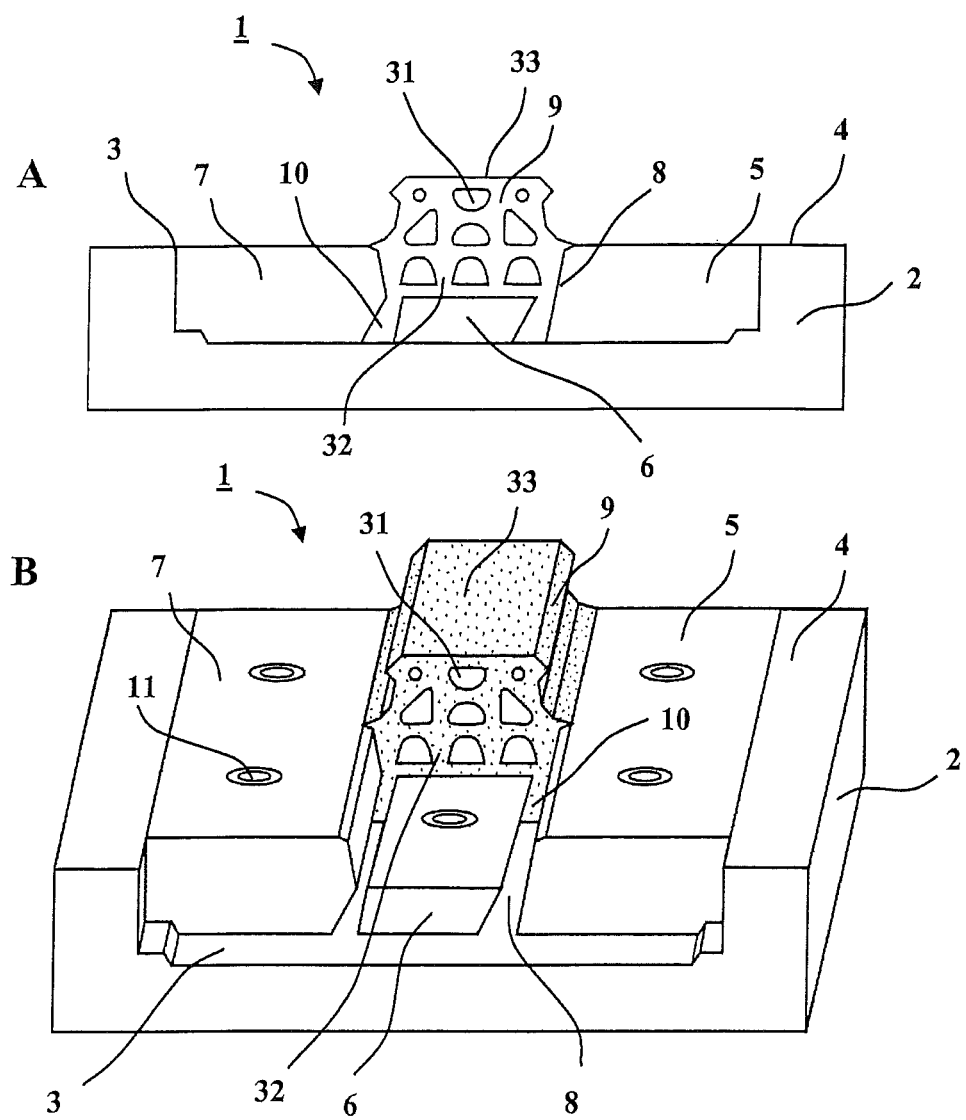
FIG. 1 shows a cross section (A) and a perspective view (B) of a cutout of part of an embodiment of a testing device according to the invention.

FIG. 1 exemplarily and schematically depicts part of a plate of an embodiment of the testing device according to the invention. The lower part (B) on FIG. 1 shows a perspective view of a cutout from a plate 2 of an embodiment of a testing device 1 according to the invention, while the upper part (A) shows a cross section through this plate 2. A recess 3 is introduced into a plate 2, for example which can be made out of metal or even some suitable plastic, e.g., polyoxymethylene (POM), polytetrafluoroethylene (PTFE) or polyetheretherketone (PEEK). The recess 3 has inserted into it a set of plate elements 5, 6, 7, which together are configured so as to fill the recess 3 in such a way as to give the latter the shape of a groove 8 that is adjusted to the base 32 of a strand-shaped sealing profile 9 with anchoring feet 10. To provide a clearer illustration, the seal 9 and plate elements 5, 6, 7 have here been partially removed. The seal 9 here involves a strand-shaped tubbing segment seal basically known from prior art. The seal 9 has two anchoring feet 10, which proceed from the profile base 32 of the seal 9 and are encased by the plate elements 5, 6, 7 in such a way as to positively retain the seal 9. Also present are hollow spaces 31 running in the longitudinal direction of the seal 9. As a rule, this type of seal 9 consists of a suitable elastomer, for example EPDM, SBR or the like. The plate elements 5, 6, 7 are detachably secured in the recess 3 by corresponding fastening devices 11. In this embodiment, in which a seal 9 with two anchoring feet 10 is present, three plate elements 5, 6, 7 are on hand, wherein a central plate element 6 is arranged between two outer plate elements 5, 7. The surfaces of the plate elements 5, 6, 7 facing toward the seal 9 are configured in such a way as to reproduce the outer shape of the profile base 32 of the seal 9. In order to incorporate the seal 9, the central plate element 6 can first be arranged and fixed in the recess 3, for example. The seal 9 can then be placed on the central plate element 6. The shape of the central plate element 6 is adjusted to the shape of the respective seal 9, i.e., the cross section of the central plate element 6 is selected in such a way that the seal 9 with its base 32 and the interior sides of the anchoring feet 10 abut against the central plate element 6. Finally, the two outer plate elements 5, 7 can be inserted into the recess 3 and fixed in place. The shape of these plate elements 5, 7 also corresponds to the outer shape of the profile base 32 and anchoring feet 10 of the seal 9, i.e., the surfaces of the plate elements 5, 7 facing toward the seal 9 are designed complementary to the outer shape of the profile base 32 and anchoring feet 10 of the seal 9. After the outer plate elements 5, 7 have been incorporated, the seal 9 is anchored in the plate 2 by a positive-locking fit. The edges of the recess 3 here also exhibit ledges, which are intended to additionally counteract a sliding of the outer plate elements 5, 7 under a load, and provide centering to achieve an optimal positive-locking fit. The outer plate elements 5, 7 here abut against the outer walls of the recess 3. Apart from the groove 8, the plate elements 5, 6, 7 thus fill the recess 3 completely in this exemplary embodiment. For example, two such plates 2 each with a respective linear strand-shaped seal 9 inserted therein can be pressed against each other for testing the force-distance behavior of the seal(s) 9.

Figure 2:
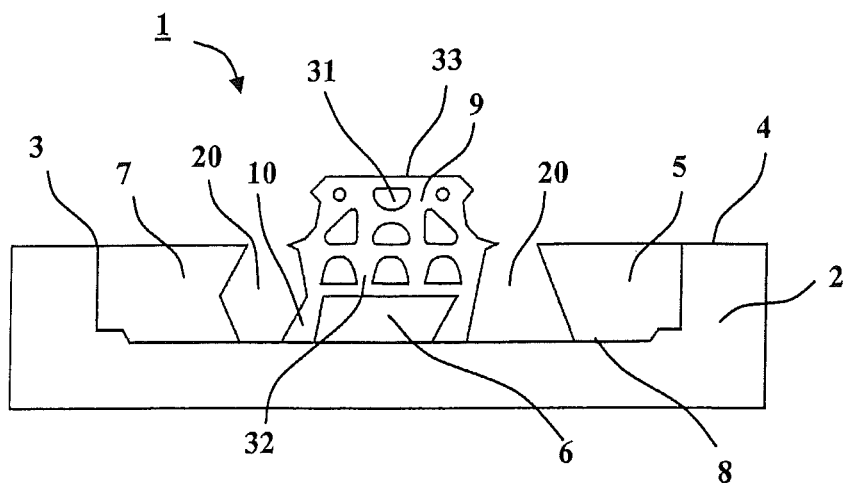
FIG. 2 shows a cross section through a part of an alternative configuration of a testing device according to the invention.
Figure 2:
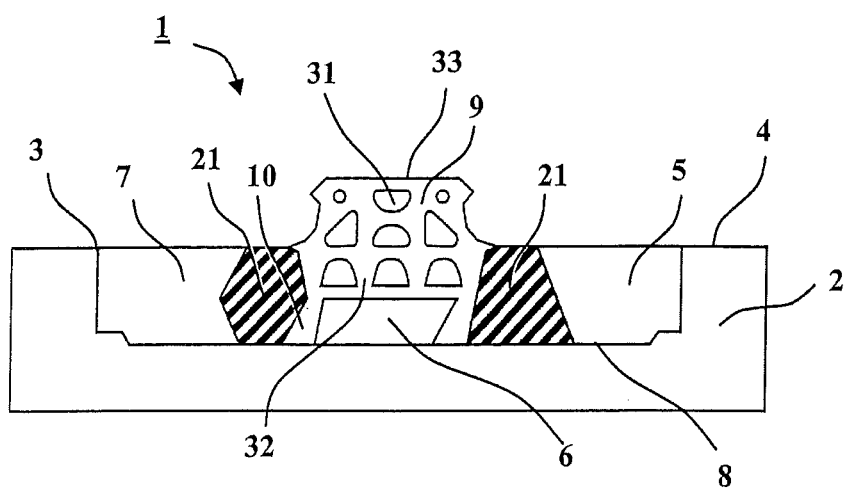

FIG. 2 shows a cross section through a plate 2 of an alternative embodiment of the testing device 1 according to the invention. The same reference numbers correspond to the same elements of the embodiment shown on FIG. 1, so that unnecessary repetition will be avoided. In this alternative embodiment, the groove 8 is not formed by the plate elements 5, 6, 7 in such a way as to reproduce the geometry of the sealing base 32, but rather the groove 8 is configured by the plate elements 5, 6, 7 in such a way as to yield a space 20 on both sides of the seal 9, which is depicted on FIG. 2A in an unfilled state, and on FIG. 2B in a state filled with a curing/curable material 21. For illustrative purposes, the outer plate elements 5, 7 are shown in different configurations. The plate element 5 exhibits an undercut, while the plate element 7 exhibits a recess with a wedge-shaped cross section. These or similar shapes ensure that the curing/curable material 21 is at least also held positively by the plate elements 5, 7 after cured. The seal 9 is embedded in the material 21, and as a whole is held in a positive-locking manner by the positive fit between the plate elements 5, 6, 7 and the cured material 21 on the one hand, as well as between the cured material 21 and the anchoring feet 10 on the other. For example, the material 21 can be concrete, making it possible to reconstruct the installation situation in a concrete component, e.g., a concrete tubbing segment, in an especially realistic manner. In order to manufacture this alternative embodiment of the testing device 1 according to the invention, the plate elements 5, 6, 7 can be secured in the recess 3, e.g., via bolting or adhesive bonding. The seal 9 is then placed on the central plate element 6. Alternatively, the outer plate elements 5, 7 can also be fixed after the seal 9 has been placed on the central plate element 6. The curing/curable material 21 is then introduced, e.g., cast, into the space 20. The material 21 either cures under normal conditions by itself, or it is cured through exposure to outside factors, e.g., under UV light and/or heating. After curing, the testing device 1 is ready for use.

Figure 3:
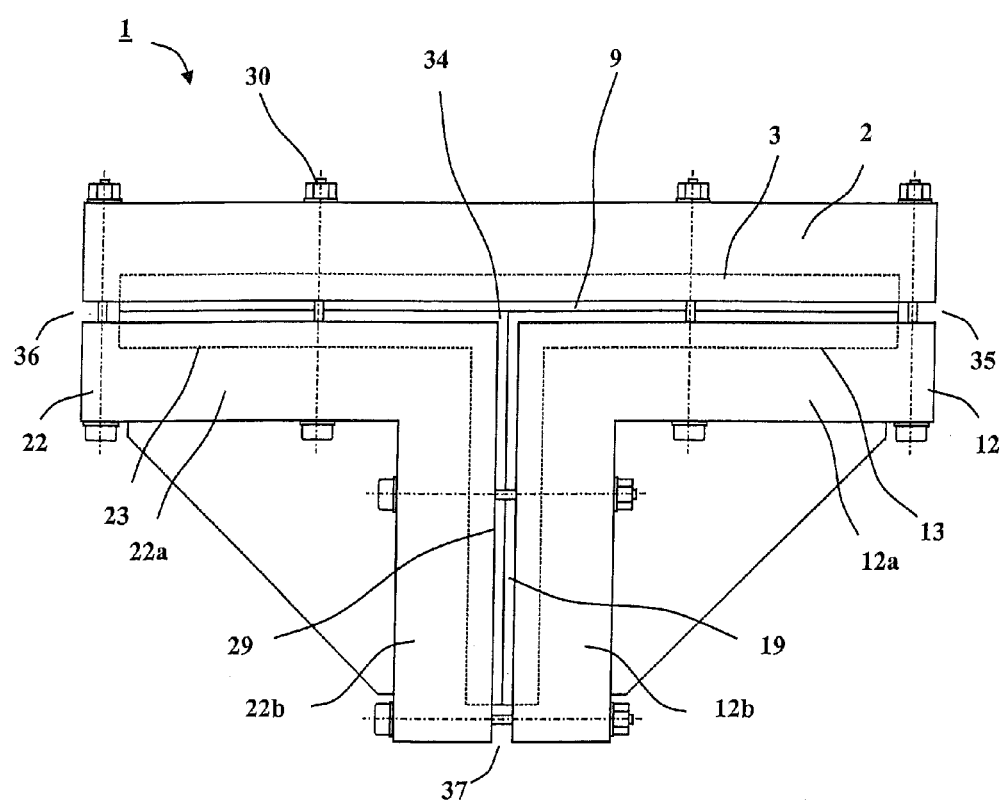
FIG. 3 shows a T-joint testing device according to the present invention.

FIG. 3 schematically depicts an embodiment of a testing device according to the invention for testing seals with anchoring feet constructed with T-joints. This testing device involves simulating an installation situation of the kind often encountered in particular in tunnel construction, when tubbing segments abut against each other in such a way that the ring and longitudinal joints meet, forming T-shaped joints. The testing device 1 according to this embodiment encompasses three plates 2, 12, 22, the structure of which in principle corresponds to the one on FIG. 1. However, two of the three plates 2, 12, 22, here the second and third plate 12, 22, are designed as angle plates with essentially an L-shaped cross section. The angle plates 12, 22 exhibit two legs 12a, b, 22a, b situated on each other at a right angle, and each abut against each other with the surfaces 14b, 24b of one leg 12b, 22b, and against the surface 4 of the planar first plate 2 with the respective other leg 12a, 22a, thereby resulting in an essentially T-shaped structure. Of course, the plates 12, 22 can also exhibit a square cross section, for example. It is only critical that the recesses 13, 23 be present in the two angled surfaces 14a, b, 24 a, b. The planar first plate 2 forms a kind of cover that preferably completely covers the surfaces 14a, 24a (see FIG. 3) of the angle plates 12, 22. Each of the plates 2, 12, 22 exhibit what is here a respective frame-like, i.e., rectangular recess 3, 13, 23, in which respective plate elements 5, 6, 7, 15, 16, 17, 25, 26, 27 (see FIG. 3) are arranged. The plate elements 5, 6, 7, 15, 16, 17,

25, 26, 27 can consist of a single piece or be assembled out of several parts. Respective frame-like seals 9, 19, 29 are inserted in the grooves 8, 18, 28 formed by the plate elements 5, 6, 7, 15, 16, 17, 25, 26, 27, and anchored as described above for FIG. 1.

The seal 9 inserted in the first plate 2 is planar, while the seals 19, 29 inserted into the second plate 12 and third plate 22 are angled to reflect the angular structure of the plates 12, 22 or recesses 3, 13, thereby forming real frame corners 34. The sealing surfaces 33 of the seals 9, 19, 29 here come to lie one on top of the other, wherein it is also possible to set a specific offset, so as to test the behavior given a seal offset. Tensioning devices 30 can be used to tension the plates 2, 12, 22 against each other, thereby pressing the seals 9, 19, 29 against each other. This testing device 1 is suitable for tightness checks, wherein a fluid, e.g., water, can be guided into the testing device 1 via suitable devices (not shown here), e.g., which can encompass boreholes through at least one of the plates 2, 12, 22, so as to apply a suitable pressure to the seals 9, 19, 29. The arrangement can also be configured for use in testing the force-distance behavior on the frame corner. In this case, the recesses 3, 13, 23 and grooves 8, 18, 28 are preferably not frame-like, but linear in design, and serve to accommodate a corresponding sealing profile strip. In this case, the open ends 35, 36, 37 of the testing device 1 are preferably sealed by end plates (not shown).

Figure 4:
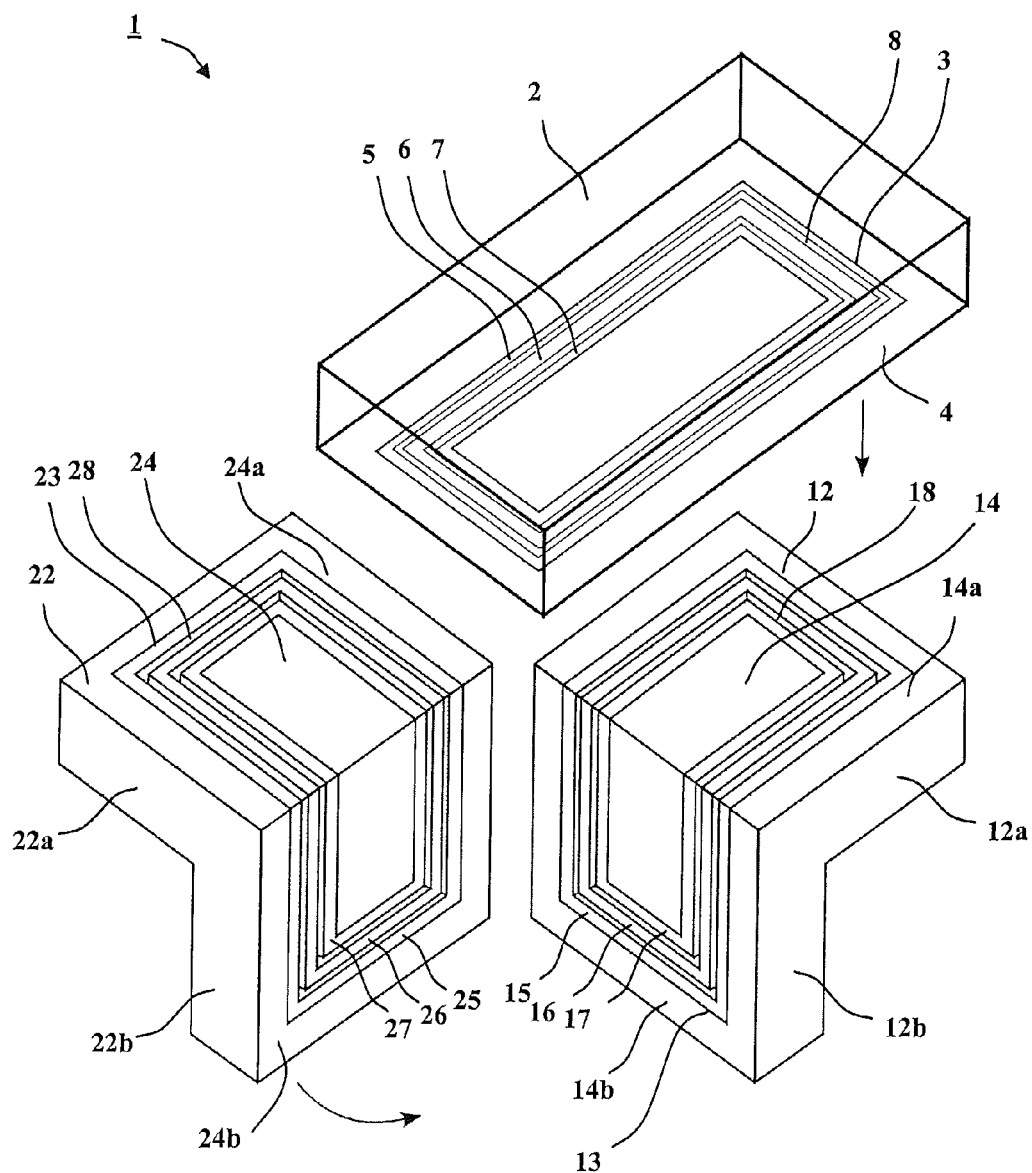
FIG. 4 shows a perspective view of the T-joint testing device from FIG. 2.

FIG. 4 presents the testing device shown on FIG. 3 in a simplified spatial view. The frame-like seals 9, 19, 29 are not depicted. The plates 2, 12, 22 with the plate elements 5, 6, 7, 15, 16, 17, 25, 26, 27 inserted into the recesses 3, 13, 23 and forming the grooves 8, 18, 28 are shown. Arrows denote how the testing device 1 is assembled after the seals 9, 19, 29 have been inserted. Tensioning devices 30, boreholes for supplying a fluid for the tightness check, etc., are not illustrated to provide a better overview.

The invention claimed is:

1. A testing device for testing seals with at least one anchoring foot, wherein
   a. the testing device comprises at least a first plate with a first surface exhibiting a first recess, and at least a second plate with a second surface exhibiting a second recess, wherein the surfaces of the plates lie essentially opposite each other at least partially with their recesses, and
   b. at least two respective plate elements are detachably secured in the first and second recess, wherein the plate elements are configured and arranged in such a way that they form a respective groove in the recesses, in which a seal exhibiting at least one anchoring foot can be inserted, such that
   i. the seal is anchored by means of a positive-locking fit formed between the plate elements and the at least one anchoring foot, or
   ii. a space is formed between the plate elements and the at least one anchoring foot of the seal, into which a curing or curable material can be incorporated, so that, after the material has cured, the seal is anchored by means of a positive-locking fit formed between the plate elements, the cured material and the at least one anchoring foot.

2. The testing device according to claim 1, wherein respective two outer plate elements and a central plate element situated in between are detachably secured in the first and second recess, and wherein the plate elements are configured in such a way as to form a respective groove in the recesses, in which a seal exhibiting two anchoring feet can be inserted in such a way as to be anchored by means of a positive-locking fit formed between the plate elements and anchoring feet, or a space is formed between the two outer plate elements and the flanks of the two anchoring feet facing them, into which the curing or curable material can be introduced, so that, after the material has cured, the seal is anchored by means of a positive-locking fit formed between the plate elements, the cured material and the anchoring feet.

3. The testing device according to claim 1, wherein the testing device encompasses at least three plates, wherein the first plate is planar, and the second and third plates are angled, so that the second and third plates each exhibit two legs situated at a right angle to each other, and wherein the second and third plates are arranged in such a way that the surfaces of the one leg face each other, and the surfaces of the other leg face the surface of the first plate.

4. The testing device according to claim 1, with seals inserted into the grooves.

5. The testing device according to claim 1, wherein the plate elements are designed as a single piece or multiple pieces.

6. The testing device according to claim 1, wherein the curing or curable material is concrete, synthetic resin or adhesive.

7. The testing device according to claim 1, wherein the testing device exhibits arrangements with which the plates can be tensioned against each other.

8. Use of a testing device according to claim 1 for performing tightness checks or testing the force-distance behavior of seals with anchoring feet, in particular tubbing segment seals, constructed with T-joints or cross-joints.

9. A method for testing seals with anchoring feet, in particular tubbing segment seals, constructed with T-joints or cross-joints, wherein a seal exhibiting at least one anchoring foot is anchored in a testing device according to claim 1, and is subjected to a tightness or force-distance behavior test.

* * * * *